US007016727B2

(12) United States Patent
Powers et al.

(10) Patent No.: US 7,016,727 B2
(45) Date of Patent: Mar. 21, 2006

(54) CARTRIDGE HAVING A POWER SOURCE AND ELECTRODE PAD FOR DEFIBRILLATOR HAVING A RECHARGEABLE BATTERY

(75) Inventors: Daniel J. Powers, Issaquah, WA (US); James K. Russell, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 850 days.

(21) Appl. No.: 09/993,841

(22) Filed: Nov. 5, 2001

(65) Prior Publication Data

US 2005/0159782 A1    Jul. 21, 2005

(51) Int. Cl.
 *A61N 1/39* (2006.01)
(52) U.S. Cl. .......................................... 607/5; 607/142
(58) Field of Classification Search ................ 607/115, 607/142, 5; 206/438, 210, 363, 370, 569, 206/570, 572, 557–558, 561, 568, 828; 600/372, 600/386; D3/203.1, 203.3; 320/101, 103
See application file for complete search history.

(56) References Cited

U.S. PATENT DOCUMENTS

| 4,832,032 | A | | 5/1989 | Schneider ................ 128/419 R |
| 5,470,343 | A | * | 11/1995 | Fincke et al. .................... 607/5 |
| 5,607,454 | A | | 3/1997 | Cameron et al. |
| 5,641,585 | A | * | 6/1997 | Lessing et al. ................ 429/26 |
| 5,658,316 | A | * | 8/1997 | Lamond et al. ................. 607/5 |
| 5,735,879 | A | | 4/1998 | Gliner et al. |
| 5,797,969 | A | * | 8/1998 | Olson et al. .................... 607/5 |
| 5,836,993 | A | | 11/1998 | Cole |
| 5,879,374 | A | | 3/1999 | Powers et al. |
| 5,967,817 | A | | 10/1999 | Greenstein ................... 439/205 |
| 6,397,104 | B1 | * | 5/2002 | Miller et al. .................... 607/5 |
| 6,586,850 | B1 | * | 7/2003 | Powers ......................... 307/85 |
| 6,591,135 | B1 | * | 7/2003 | Palmer et al. .................. 607/5 |
| 6,662,056 | B1 | * | 12/2003 | Picardo et al. .............. 607/142 |
| 2003/0114885 | A1 | * | 6/2003 | Nova et al. ..................... 607/2 |
| 2003/0197487 | A1 | * | 10/2003 | Tamura et al. .............. 320/114 |
| 2003/0201752 | A1 | * | 10/2003 | Locke et al. ................. 320/111 |

FOREIGN PATENT DOCUMENTS

GB            2 351 912 A        1/2001

* cited by examiner

*Primary Examiner*—George Manuel
*Assistant Examiner*—Nicole R. Kramer
(74) *Attorney, Agent, or Firm*—Tony Piotrowski

(57) ABSTRACT

An automated or semi-automated defibrillator (AED) system includes an AED and a cartridge attachable to the AED. The cartridge includes electrode pads and a power source such as a battery or fuel cell, which may recharge a defibrillator battery, power defibrillator circuitry, or both. Because the cartridge includes both a power source and electrode pads, one can replace the power source and the pads at the same time by replacing a single cartridge. Furthermore, in defibrillator systems where the power source charges the defibrillator battery, the power source can be selected to have the same life as the pads, thus making it practical to replace the power source and pads at the same time. In addition, maintenance for such a charging defibrillator system typically costs less than for a non-charging system because it often costs less to replace the power source than to replace the defibrillator battery.

9 Claims, 8 Drawing Sheets

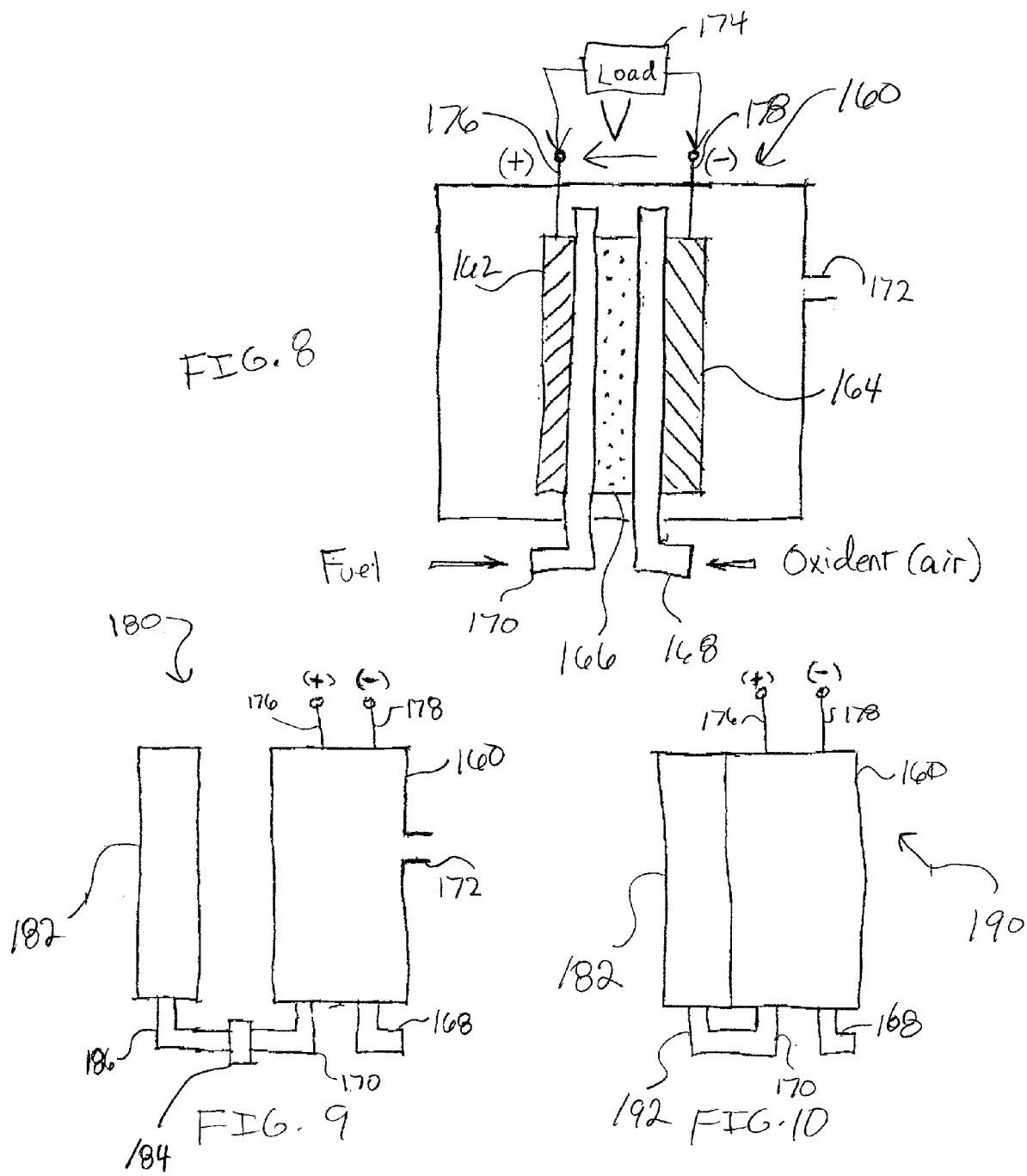

CARTRIDGE HAVING A POWER SOURCE AND ELECTRODE PAD FOR DEFIBRILLATOR HAVING A RECHARGEABLE BATTERY

FIELD OF THE INVENTION

The invention relates generally to a medical device such as an automated or semi-automated external defibrillator (AED), and more particularly to a pad cartridge for storing a power source and an electrode pad, a defibrillator having a rechargeable battery, a defibrillator system having a single field-replaceable component, and related methods.

BACKGROUND OF THE INVENTION

AEDs have saved many lives in non-hospital settings, and, as a result of advances in AED technology, the number of lives saved per year is rising. An AED is a battery-operated device that analyzes a patient's heart rhythm, and, if appropriate, administers an electrical shock (automated) or instructs an operator to administer an electrical shock (semi-automated) to the patient via electrode pads. For example, such a shock can often revive a patient who is experiencing ventricular fibrillation (VF).

As discussed below in conjunction with FIG. 1, AEDs often require periodic maintenance by the customer, i.e., "in the field". For example, one typically replaces the electrode pads after each use or after a specified period of nonuse, and replaces the battery when it is depleted.

Unfortunately, AEDs often require different types of field maintenance at different intervals, and some types of field maintenance are relatively expensive. For example, the life of the electrode pads is typically unrelated to the life of the battery. Therefore, one typically replaces the pads and the battery at different times. Furthermore, because of the power requirements of an AED, a replacement battery is often relatively expensive.

FIG. 1 is a perspective view of a conventional AED system 10, which includes an AED 12 for generating a defibrillation shock, defibrillator electrode pads 14a and 14b for providing the shock to a patient (not shown), and a battery 15. A connector 16 couples the electrode pads 14a and 14b to a receptacle 18 of the AED 12. Typically, the electrode pads 14a and 14b are sealed within a flexible, i.e., soft, package (not shown) that an operator (hands shown in FIG. 1) tears or peels open to access the electrode pads 14a and 14b. The package acts as a moisture barrier that prevents the electrode-pad contact gel (not shown) from prematurely drying out during storage of the electrode pads 14a and 14b. The battery 15, which typically is a lithium-ion battery, can provide relatively high power so that the AED 12 can quickly generate the defibrillation shock. The battery 15 and AED 12 may be stored separately, with the operator connecting the battery 15 to the AED 12 just prior to use in an emergency. Or preferably, the battery 15 and AED 12 may be stored together, with the battery 15 connected to the AED 12 during storage.

The AED 12 includes a main on/off key switch 22, a display 24 for displaying operator instructions, cardiac waveforms, or other information, a speaker 26 for providing audible operator instructions or other information, an AED status indicator 28, and a shock button 30, which the operator presses to deliver a shock to the patient (not shown). The AED 12 may also include a microphone 32 for recording the operator's voice and other audible sounds that occur during the rescue, and a data card 34 for storing these sounds along with the patient's ECG and a record of AED events for later study.

Still referring to FIG. 1, during an emergency where it is determined that the patient (not shown) may need a shock, the operator retrieves the AED 12 and installs the battery 15 if it is not already installed. Next, the operator removes the electrode pads 14a and 14b from the protective package (not shown) and inserts the connector 16 into the receptacle 18. Then, the operator turns the on/off switch 22 to the "on" position to activate the AED 12. Following the instructions displayed on the display 24 or "spoken" via the speaker 26, the operator places the electrode pads 14a and 14b on the patient in the respective positions shown in the pictures on the pads and on the AED 12. After the operator places the electrode pads 14a and 14b on the patient, the AED 12 analyzes the patient's ECG to determine whether the patient is suffering from a shockable heart rhythm. If the AED 12 determines that the patient is suffering from a shockable heart rhythm, then it instructs the operator to depress the shock button 30 to deliver a shock to the patient. Conversely, if the AED 12 determines that the patient is not suffering from a shockable heart rhythm, it informs the operator to seek appropriate non-shock treatment for the patient and often disables the shock button 30 so that even if the operator presses the button 30, the AED 12 does not shock the patient.

The AED system 10 typically requires periodic field maintenance to ensure that it is ready for emergency use at all times. Specifically, one replaces the battery 15 when the AED 12 determines that the charge stored in the battery has fallen below a predetermined level. If the AED system 10 delivers no more than a few defibrillation shocks while a particular battery 15 is installed, then this battery usually lasts for approximately five years before leakage or power drawn by the AED 12 (e.g., during periodic self-tests) drains the battery. Furthermore, one typically replaces the pads 14a and 14b after use—merely opening the pad package (not shown) typically constitutes use—or when they are no longer viable. For example, if the pads 14a and 14b are unopened, they usually have a shelf life of one to three years before the contact gel (not shown) dries out or the pads otherwise degrade from heat exposure or other causes.

Unfortunately, because it is impractical to perform all of the field maintenance at the same time, one typically performs different aspects of the maintenance at different times. For example, if the AED system 10 is not used, then one typically replaces the pads 14a and 14b every one to three years and replaces the battery 15 every five years. Although one could eliminate separately replacing the battery 15 by prematurely replacing the battery whenever he/she replaces the pads 14a and 14b, the high cost (approximately $80–$100) of the battery 15 makes this impractical.

Consequently, a need exists for an AED system that makes it more practical to perform different aspects of the field maintenance at the same time. Furthermore, a need exists for an AED system that allows one to perform different aspects of the field maintenance by replacing a single component. In addition, a need exists for an AED system that reduces the cost of maintenance.

SUMMARY OF THE INVENTION

In one embodiment of the invention, a defibrillator system includes a defibrillator and a cartridge attachable to the defibrillator. The cartridge includes an electrode pad and a power source such as a battery, which may recharge a defibrillator battery, power defibrillator circuitry, or both.

Because the cartridge includes both a power source and an electrode pad, one can replace the power source and the pad at the same time by replacing a single cartridge. Furthermore, in defibrillator systems where the power source charges the defibrillator battery, the power source can be selected to have approximately the same life as the pad, thus making it practical to replace the power source and pad at the same time. In addition, maintenance for such a charging defibrillator system typically costs less than for a non-charging defibrillator system because it is often less expensive to replace the power source than to replace the defibrillator battery.

BRIEF DESCRIPTION OF THE DRAWINGS

FIG. 8 is a diagram of a fuel cell that can be used in place of one or more batteries of FIGS. 2–5 according to an embodiment of the invention.

FIG. 9 is a diagram of a fuel-cell system that includes the fuel cell of FIG. 8 according to an embodiment of the invention.

FIG. 10 is a diagram of a fuel-cell system that includes the fuel cell of FIG. 8 according to another embodiment of the invention.

DESCRIPTION OF THE PREFERRED EMBODIMENTS

The following discussion is presented to enable a person skilled in the art to make and use the invention. Various modifications to the embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. Furthermore, for purposes of the application, "a self-contained power source" is a power source, such as a battery, fuel cell, or solar cell, that can provide power without a connection to power mains such as an AC outlet.

Figure 1:
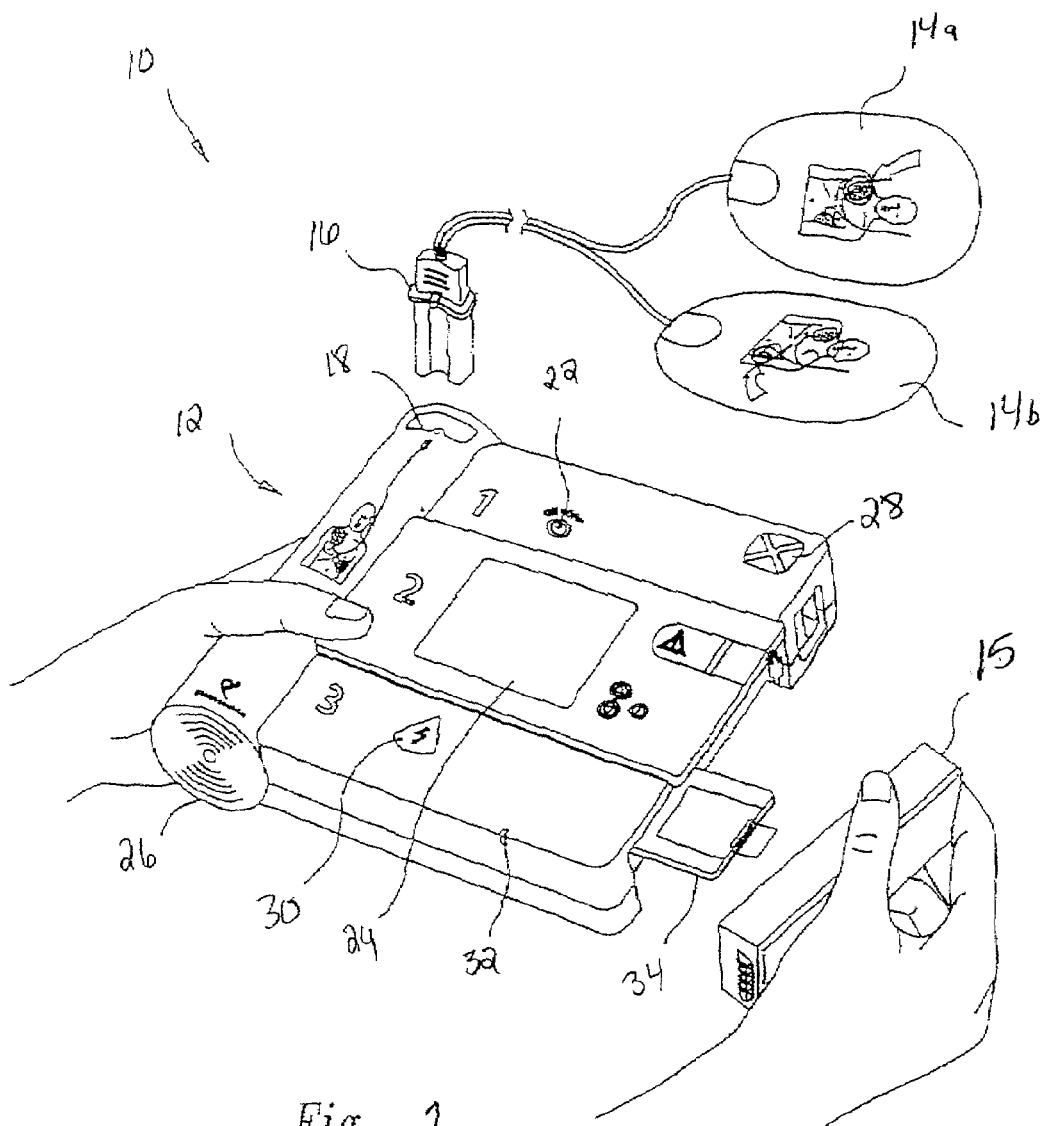
FIG. 1 is a perspective view of a conventional AED system.
Figure 2:
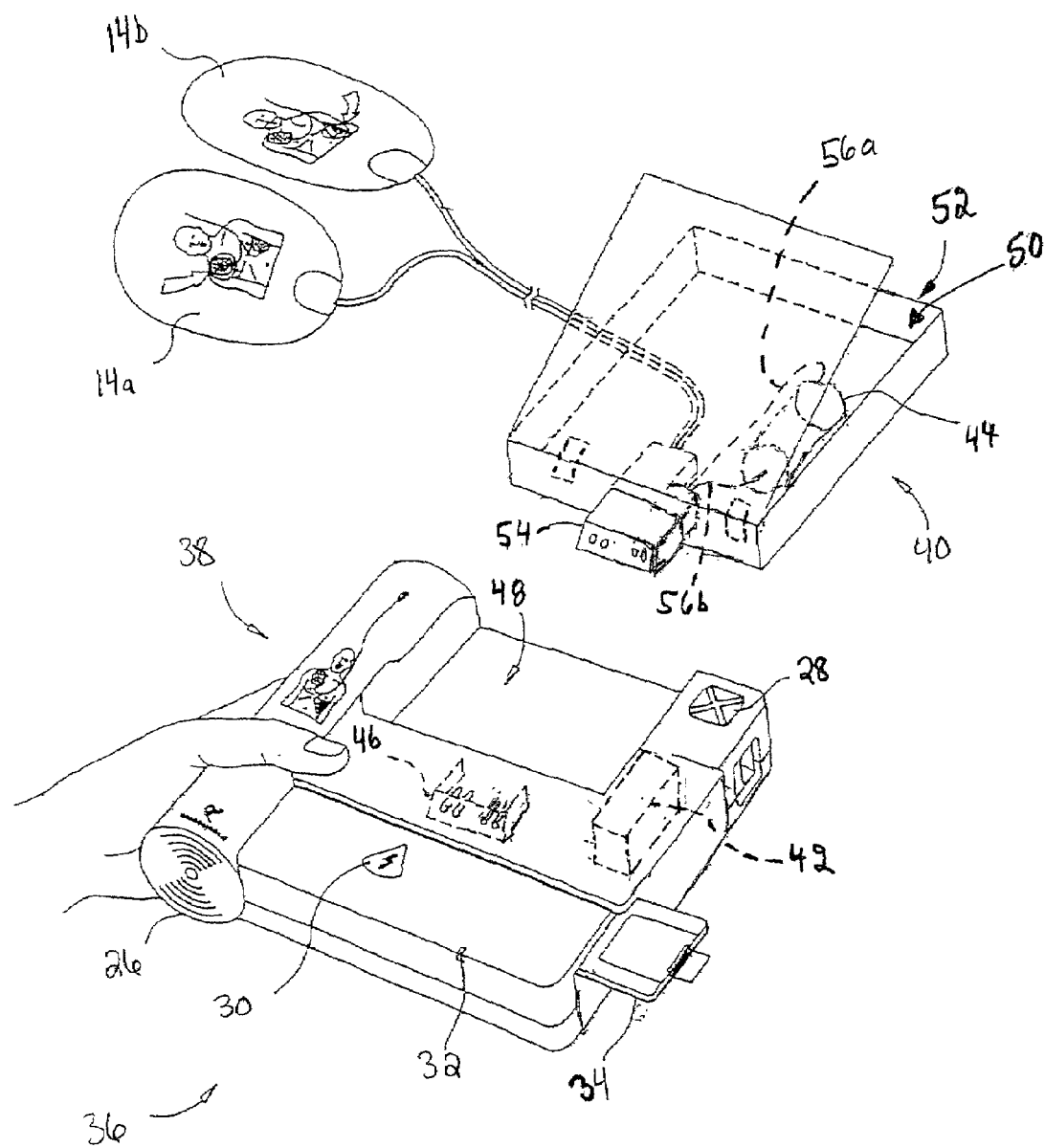
FIG. 2 is a perspective view of an AED system having a pad/power-source cartridge and a rechargeable AED according to an embodiment of the invention.

FIG. 2 is a perspective view of an AED system 36 that includes an AED 38 and a pad/power-source cartridge 40 according to an embodiment of the invention, where like numerals in FIGS. 1 and 2 refer to like elements in the systems 10 and 36. The AED 38 includes a rechargeable defibrillator battery 42, and the cartridge 40 includes a self-contained power source, here a battery 44, that charges the battery 42. Consequently, one need only replace the cartridge 40 for routine field maintenance. Furthermore, the cost of this maintenance is often reduced because the battery 44 is typically much less expensive than the defibrillator battery 42.

The AED 38 includes the rechargeable battery 42, a connector 46, a receptacle 48 for receiving the cartridge 40, and other features discussed above in conjunction with FIG. 1.

The battery 42 charges the AED's shock circuitry (FIG. 6) when the AED 38 determines that a patient (not shown) requires a shock, and also powers the remaining circuitry during treatment of the patient and during periodic self tests of the AED. To charge the shock circuitry relatively quickly—typically within a few seconds—the battery 42 should be able to generate a relatively high charging current. Furthermore, to power the AED during periodic self tests over a relatively long period of time—typically 3–5 years or more—the battery 42 should have relatively low leakage and have a relatively long life. Moreover, to reduce maintenance costs, the battery 42 should be rechargeable. Consequently, the battery 42 is typically a lithium-ion battery, although the battery 42 may be a nickel-cadmium or other type of battery that has the desired characteristics. Although shown disposed within the AED 38, the battery 42 may be disposed outside of the AED as shown in FIG. 1. In addition, although the battery 42 may be field replaceable, one typically sends the AED 38 back to the manufacture for replacement of the battery 42, or discards the AED, when the battery 42 can no longer hold a charge. Moreover, although on battery 42 is shown, the AED 38 may include multiple batteries 42.

Regarding the connector 46 and the receptacle 48, similar connectors and receptacles, as well as other techniques for attaching the cartridge 40 to the AED 38, are discussed in U.S. patent application Ser. No. 09/852,431, entitled CARTRIDGE FOR STORING AN ELECTRODE PAD AND METHODS FOR USING AND MAKING THE CARTRIDGE, which is incorporated by reference.

And although shown as lacking the on/off switch 22 and display 24, the AED 38 may include these features. But, to accommodate the connector 46 and receptacle 48, the switch 22 and the display 24 may be displaced from their respective locations on the AED 12 of FIG. 1.

Still referring to FIG. 2, the cartridge 40 includes a compartment 50 for storing the electrode pads 14a and 14b and the charging battery 44, a lidded housing 52 that defines the compartment 50, a connector 54 that mates with the connector 46 when the housing 52 is disposed within the receptacle 48, and leads 56a and 56b that connect the battery 44 to the connector 54. In one embodiment, the battery 44 is a low-cost disposable battery such as a zinc-carbon, zinc-mercury, or zinc-manganese, i.e., alkaline, battery. Such a battery typically stores a relatively high amount of energy when fresh and costs less than $1.00 (U.S.). Although the battery 44 may be unable to generate a current high enough to charge the shock circuitry (FIG. 6) of the AED 38, it can recharge the battery 42. Furthermore, low-cost disposable batteries, particular alkaline batteries, have been found to have approximately the same shelf life as the pads 14a and 14b and to degrade with temperature at a rate that is similar to the pads' temperature-degradation rate. The battery 44 is coupled to the battery 42 via the connectors 46 and 54, and is conventionally secured within the compartment 50. Furthermore, the battery 44 may or may not be replaceable independently of the cartridge 40, and although one battery 44 is shown, the cartridge may store multiple batteries 44 coupled in either series or parallel. The housing 52 is typically formed from plastic and is hermetically sealed with the pads 14a and 14b and battery 44 inside. In addition, although the cartridge 40 is shown storing a pair of electrode pads 14a and 14b and storing the battery 44 inside the housing 52, the cartridge 40 may include more or fewer pads and store the battery outside the housing. Cartridges similar to the cartridge 40 (except without the battery 44) are discussed in U.S. patent application Ser. No. 09/852,431, entitled CARTRIDGE FOR STORING AN ELECTRODE PAD AND METHODS FOR USING AND MAKING THE CARTRIDGE, which is incorporated by reference.

In operation, one periodically replaces a single component—the cartridge 40—in the field to maintain the AED system 36. That is, one replaces the cartridge 40 at regular intervals to maintain a viable set of pads 14a and 14b and an adequate charge level on the defibrillator battery 42. Therefore, by allowing routine field maintenance with the replacement of a single component, the AED system 36 is relatively simple to maintain. Furthermore, because, as discussed above, the battery 44 typically costs on the order of $1/100^{th}$ of what the battery 42 costs, including the battery 44 in the cartridge 40 reduces the cost of maintaining the system 36. Moreover, although the replacement cartridge 40 includes the battery 44, the original cartridge 40 that comes with the AED system 36 may omit the battery 44 because the defibrillator battery 42 is fresh and typically has an expected life that is at least as long as the shelf life of the pads 14a and 14b.

In one embodiment, one replaces the original cartridge with a replacement cartridge 40 when the pads 14a and 14b need replacement either because they have been used or because their shelf life has expired. Once the replacement cartridge 40 is installed in the AED 38, the battery 44 recharges the battery 42 to a predetermined charge level, and thereafter maintains this charge level on the battery 42 until the battery 44 can no longer do so. As long as the battery 44 has a life that is at least as long as the pads' shelf life, one will typically replace the cartridge 40 before the battery 44 loses its ability to charge the battery 42.

In another embodiment, one replaces the original cartridge with a replacement cartridge 40 when the battery 44 needs replacement. Specifically, the AED 38 monitors the battery 44 and sounds a warning (e.g., via the speaker 26) when the charge level on the battery 44 falls below a predetermined threshold. As long as the pads 14a and 14b have a life that is at least as long as the battery's expected life, then one will typically replace the cartridge 40 before the pads expire. Furthermore, as stated above, some types of batteries such as alkaline batteries degrade with exposure to heat at a rate similar to the rate at which the pads 14a and 14b degrade with exposure to heat. Therefore, by using such a battery for the battery 44, the AED 38 can sound a warning if one should replace the cartridge 40 earlier than scheduled due to heat degradation of the pads 14a and 14b.

In yet another embodiment, one replaces the original cartridge with a replacement cartridge 40 when the battery 42 needs recharging. Specifically, the AED 38 monitors the battery 42 and sounds a warning (e.g., via the speaker 26) when the charge level on the battery 42 falls below a predetermined threshold. This indicates that the battery 44 needs to be replaced because it can no longer charge the battery 42. A potential advantage to monitoring the battery 42 instead of the battery 44 is a longer time between replacements of the cartridge 40 because the battery 44 will often discharge before the battery 42.

Still referring to FIG. 2, one or more fuel-cell systems (FIGS. 9–10) may be used in place of the battery 42. A fuel-cell system typically includes a fuel cell (FIG. 8) and a fuel reservoir connected to the cell. In one embodiment, the fuel cell is located in the AED 38 and the cartridge 40 contains the reservoir. The fuel cell uses this fuel to generate the electricity that charges the battery 44. When the fuel is or nearly is exhausted, one replaces the cartridge 40 to replenish the fuel supply. In another embodiment, both the fuel cell and the fuel reservoir are located in the cartridge 40.

Figure 3:
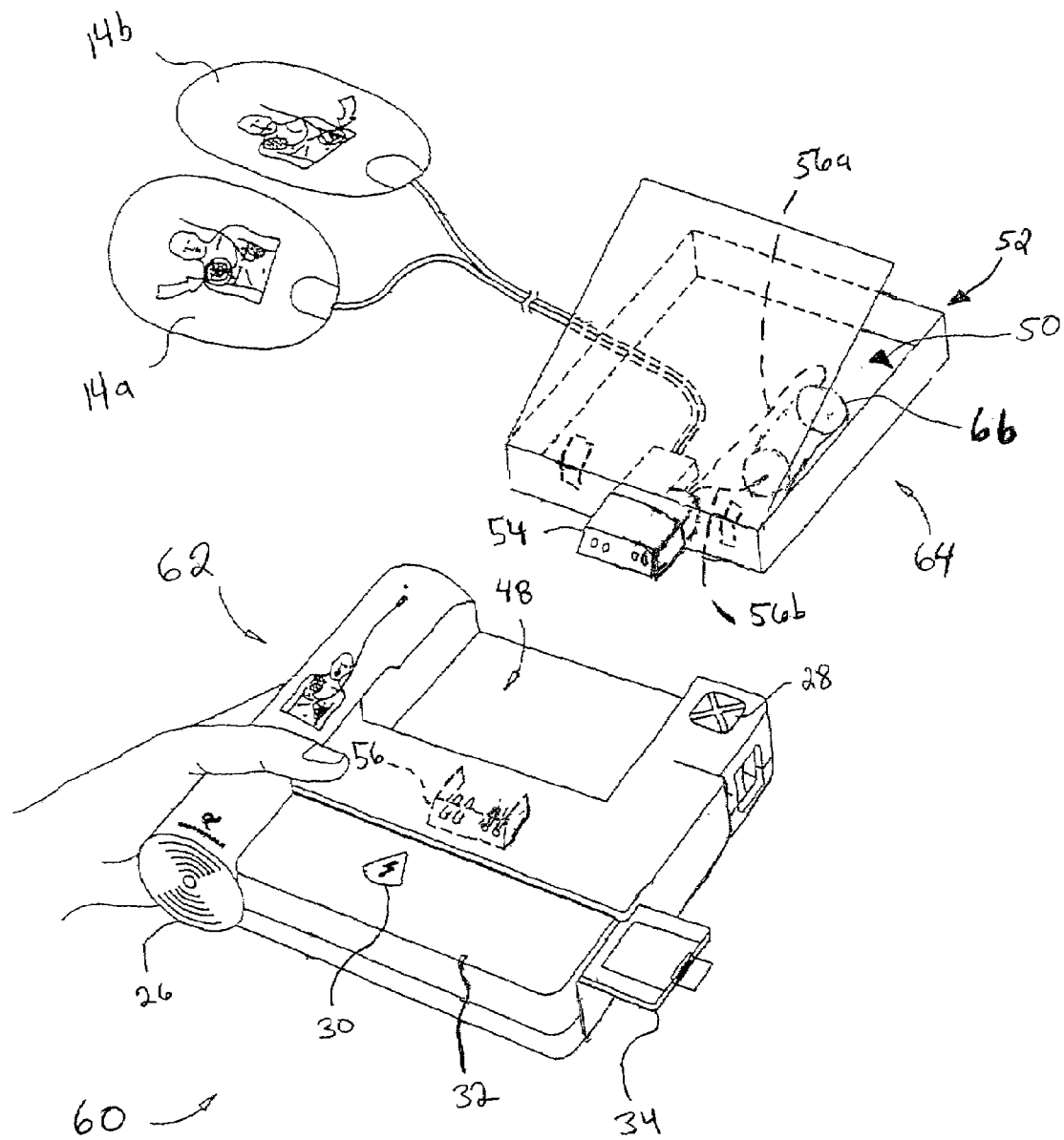
FIG. 3 is a perspective view of an AED system having a pad/power-source cartridge and a non-rechargeable AED according to an embodiment of the invention.

FIG. 3 is a perspective view of an AED system 60 that includes an AED 62 and a pad/power-source cartridge 64 according to an embodiment of the invention, where like numerals in FIGS. 2 and 3 refer to like elements in the systems 36 and 60. A major difference between the AED systems 36 and 60 is that in the system 60, the AED 62 has no battery, and a battery 66 or other power source in the cartridge 64 powers the AED 62. The battery 66 is similar to the battery 42 of FIG. 2 so that it can charge the shock circuitry (FIG. 6) relatively quickly and power the AED 62 during periodic self tests over a relatively long period of time, which is typically at least the shelf life of the pads 14a and 14b. Although the high cost of the battery 66 makes replacing the cartridge 64 more expensive than changing the cartridge 40 of FIG. 2, one does not have the added task of replacing a defibrillator battery, such as the battery 42 of FIG. 2, or discarding the AED when the defibrillator battery can no longer hold a charge. Furthermore, like the AED system 36 of FIG. 2, the AED system 60 has only one field-replaceable component, the cartridge 62. Moreover, although only one battery 66 is shown, the cartridge 64 may include multiple batteries 66.

Alternatively, one or more fuel-cell systems (FIGS. 9–10) may be used in place of the battery 66. The fuel cell (FIG. 8) and its fuel reservoir (FIGS. 9–10) may be located in the cartridge 64, or the cell may be located in the AED 62 and the reservoir located in the cartridge 64.

Figure 4:
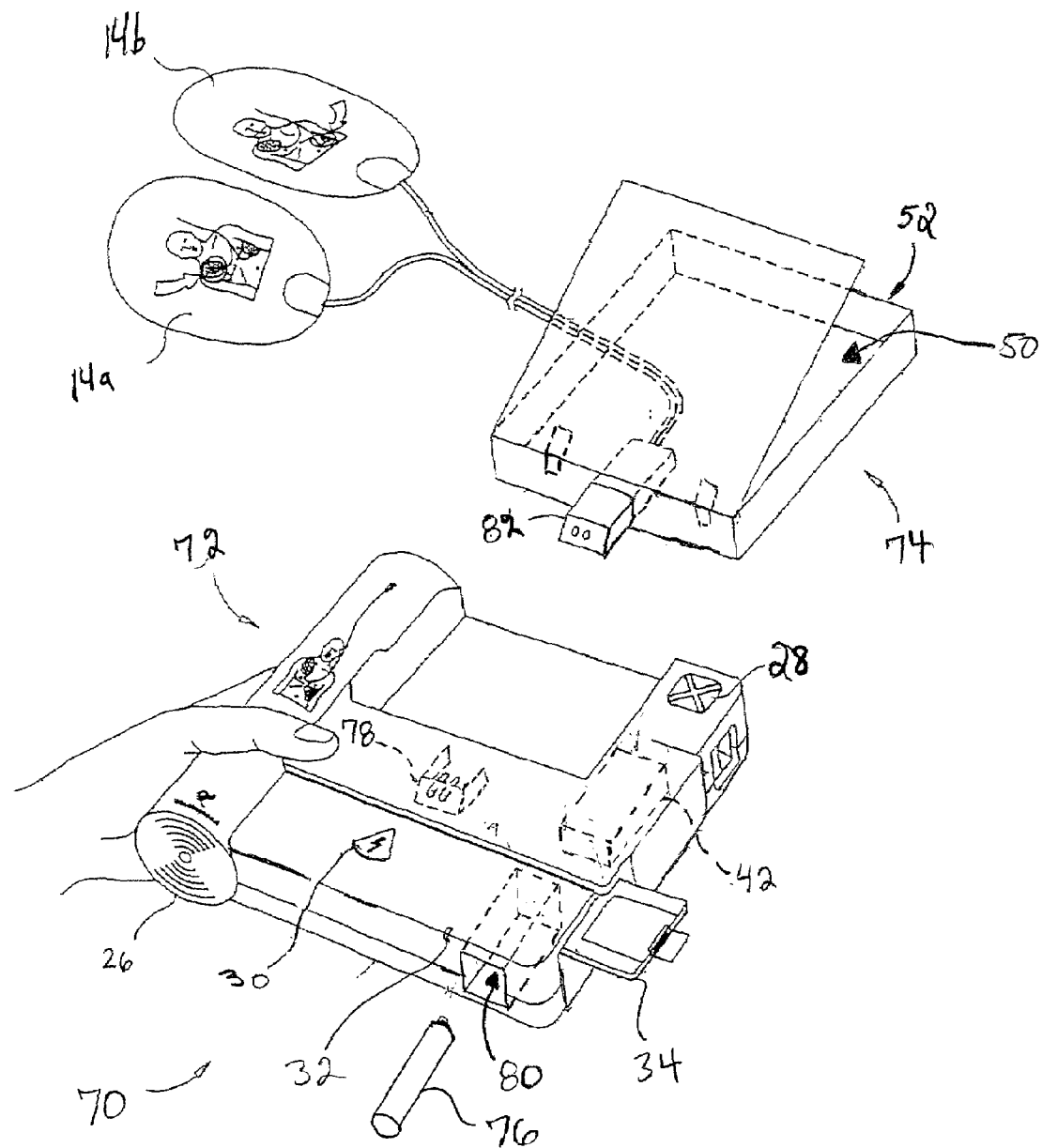
FIG. 4 is a perspective view of an AED system having a pad cartridge and a rechargeable AED according to an embodiment of the invention.

FIG. 4 is a perspective view of an AED system 70 that includes an AED 72 and a pad cartridge 74 according to an embodiment of the invention, where like numerals in FIGS. 2 and 4 refer to like elements in the systems 36 and 70. A major difference between the AED systems 36 and 70 is that in the system 70, a recharge battery 76, which is similar to the battery 44 of FIG. 2, is disposed in the AED 72, not in the cartridge 74. Although locating the recharge battery 76 away from the cartridge 74 separates replacement of the pads 14a and 14b and the recharge battery into two maintenance steps, the battery 76 reduces maintenance costs because it is less expensive to replace than the defibrillator battery 42 as discussed above in conjunction with FIG. 2. Furthermore, if the battery 76 and pads 14a and 14b do not have similar lives, maintenance costs are further reduced because one need not replace viable pads 14a and 14b just because the battery 76 needs replacing or vice versa.

The AED 72 includes the rechargeable defibrillator battery 42, recharge battery 76, a connector 78, the receptacle 48 for receiving the cartridge 74, a compartment 80 for the battery 76, and other features discussed above in conjunction with FIG. 1. As discussed above, the battery 76 is similar to the battery 44 of FIG. 2. And, if the battery 76 is of the appropriate chemistry and the AED 38 and pads 14a and 14b are stored together, the AED can detect temperature degradation of the pads by monitoring the battery 76 as discussed above in conjunction with FIG. 2. The connector 78 is similar to the connector 46 of FIG. 2 except that it does not couple a recharge battery to the defibrillator battery 42. The battery compartment 80 can have a cover (not shown) and otherwise be similar to conventional battery compartments present in battery-operated electronic devices such as portable compact-disc (CD) players (not shown). Furthermore, although shown disposed within the AED 72 and designed to hold only one battery 76, the compartment 80 may be attached to the outside of the AED or may be designed to hold multiple batteries 76 in a serial or parallel configuration.

The cartridge 74 includes a connector 82, and, except for not storing a recharge battery, is otherwise similar to the cartridge 40 of FIG. 2. The connector 82 is similar to the connector 54 of FIG. 2 except that it does not couple a recharge battery to the defibrillator battery 42.

Still referring to FIG. 4, one or more fuel-cell systems (FIGS. 9–10) may be used in place of the battery 76. When the fuel cell's fuel is or nearly is exhausted, one refills the fuel reservoir or replaces the entire fuel-cell system.

Alternatively, the battery 76 can be eliminated, and one or more fuel-cell systems (FIGS. 9–10) can be used in place of the battery 42. When the cell's fuel is or nearly is exhausted, one replaces the fuel-cell system. Alternatively, one can merely refill the fuel reservoir. Furthermore, if the fuel reservoir is large enough, the fuel cell can power the AED 72 almost indefinitely.

Figure 5:
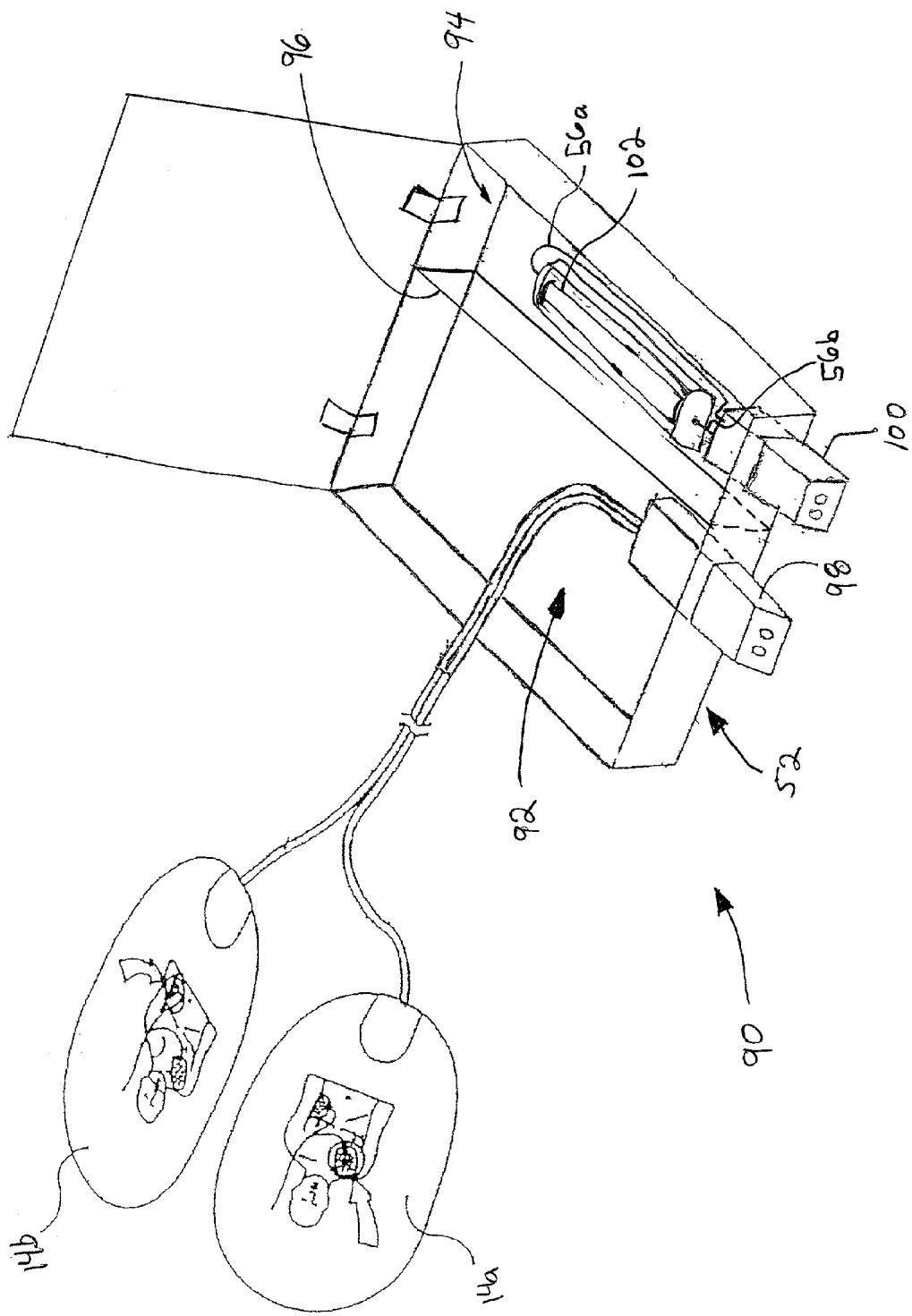
FIG. 5 is a perspective view of a pad/power-source cartridge having multiple compartments and multiple connectors according to an embodiment of the invention.

FIG. 5 is a perspective view of a cartridge 90 that may replace the cartridges 40 and 64 in the AED systems 36 and 60 of FIGS. 2 and 3, respectively, according to an embodiment of the invention, where like numerals refer to like elements of the cartridges 40, 64, and 90. A major difference between the cartridge 90 and cartridges 40 and 64 is that the cartridge 90 includes pad and battery compartments 92 and 94, which are separated by a divider 96, and includes separate pad and battery connectors 98 and 100. A battery 102 is disposed in the battery compartment 94, and may be similar to the battery 44 of FIG. 2 in that it charges a defibrillator battery, or may be similar to the battery 66 of FIG. 3 in that it powers the AED 62. Although one battery 102 is shown, the battery compartment 94 may be designed to hold multiple batteries 102 in a series or parallel configuration. Furthermore, one may use one or more fuel-cell systems (FIGS. 9–10) in place of the battery 102.

Referring to FIGS. 2, 3, and 5, to accommodate the connectors 98 and 100 of the cartridge 90, each of the AEDs 38 and 62 would be modified to include two corresponding connectors instead of one connector 46 and 56, respectively. Otherwise, the AEDs 38 and 62 would be the same as discussed above in conjunction with FIGS. 2 and 3, respectively.

Figure 6:
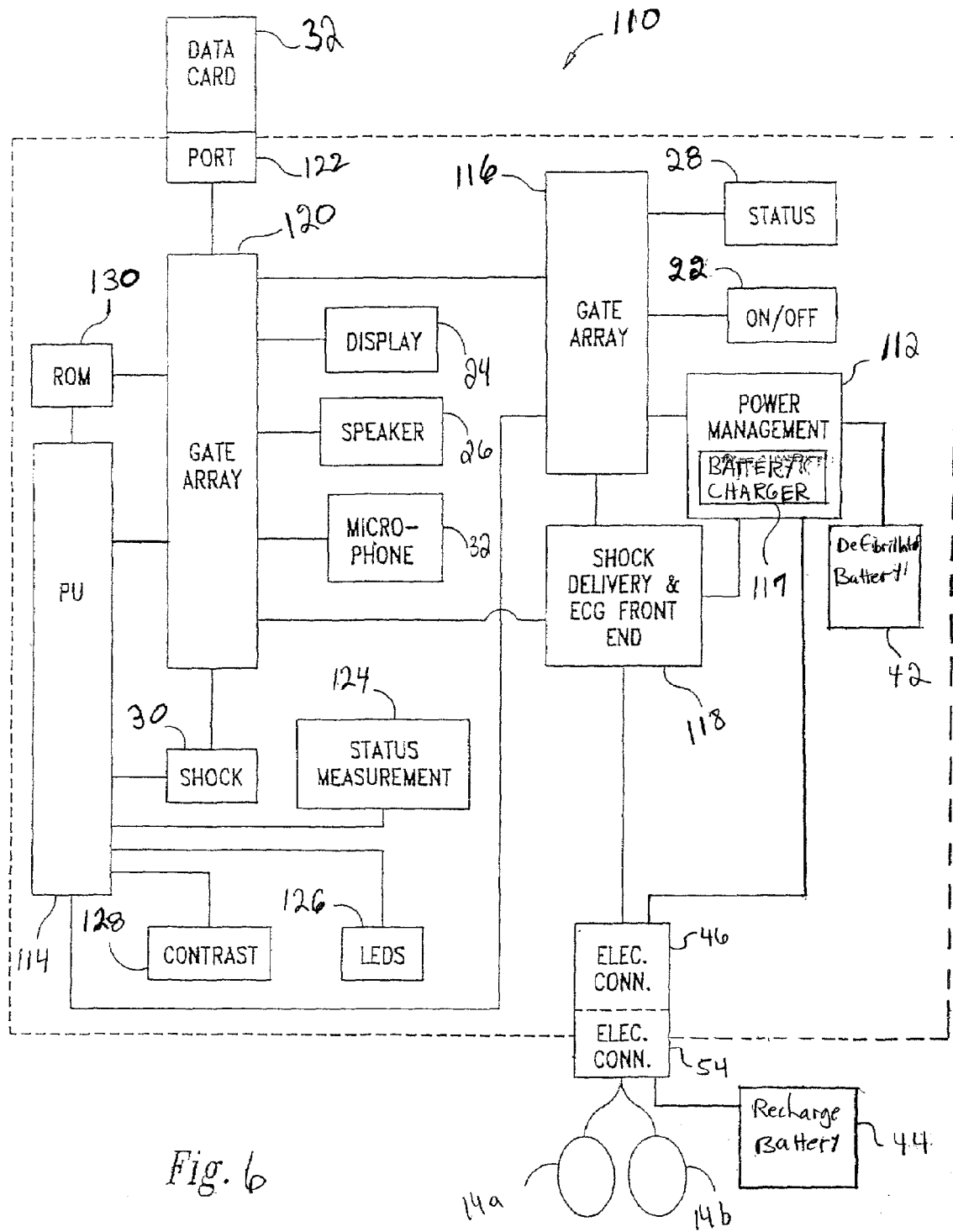
FIG. 6 is a block diagram of an AED circuit that the AEDs of FIGS. 2–4 can incorporate according to an embodiment of the invention.

FIG. 6 is a block diagram of an AED circuit 110, which the AED's 38, 62, and 72 of FIGS. 2–4, respectively, can incorporate according to an embodiment of the invention. For clarity, the circuit 110 is discussed in conjunction with the AED 38, it being understood that the discussion also applies to the circuit 110 when used in the AEDs 62 and 72 unless otherwise noted.

The AED circuit 110 includes a power management (PM) circuit 112, which interfaces with a processing unit (PU) 114 via a gate array 116, a shock-delivery-and-ECG-front-end circuit 118, the defibrillator battery 42, (which powers the circuit 110), and a recharge battery 44 (except no recharge battery in the AED 62). Under the control of the PU 114, the PM circuit 112 distributes power from the battery 42 to the other circuits of the circuit 110, and includes a battery charger 117 for charging the battery 42 with power from the battery 44. The battery charger 117 is further discussed below in conjunction with FIG. 7, and may be omitted from the AED 62 (FIG. 3) because there is no recharge battery 44. In addition, the PU 114 monitors the voltage across the battery 44 via the PM 112 and generates an alarm via the display 24, speaker 26, or other means to indicate that the battery 44, and thus the cartridge 40 (FIG. 2), needs to be replaced. Furthermore, although shown as disposed in the cartridge 40 (FIG. 2), the battery 44 may be disposed within the AED as shown for the AED 72 of FIG. 4.

The AED circuit 110 also includes the shock-delivery-and-ECG-front-end circuit 118, which, during treatment of a patient (not shown), samples the patient's ECG to determine if the patient is suffering from a shockable heart arrhythmia. The PU 114 receives the samples from the circuit 118 via a gate array 120 and analyzes them. If analysis indicates that the patient is suffering from a shockable heart rhythm, then the PU 114 instructs the circuit 118 via the gate array 120 to enable delivery of a shock to the patient when an operator (not shown) presses the shock button 30. Conversely, if analysis indicates that the patient is not suffering from a shockable heart rhythm, then the PU 114 effectively disables the shock button 30 by preventing the circuit 118 from delivering a shock to the patient when the operator presses the shock button 30.

Still referring to FIG. 6, the on/off switch 22 (FIG. 1) turns the AED circuit 110 "on" and "off" and the gate array 116 interfaces the PM circuit 112, the on/off switch 22, and the status indicator 28 to the shock-delivery-and-ECG-front-end circuit 118, the PU 114, and the gate array 120.

The circuit 110 also includes the display 24, which presents information to an operator, the speaker 26, which may provide audio instructions to the operator, and the microphone 32, which may record the operator's voice and other audible sounds. The data card 32 is connected to the gate array 120 via a port 122, and may store the operator's voice and other sounds along with the patient's ECG and a record of AED events for later study.

A status-measurement circuit 124 provides the status of the other circuits of the AED circuit 110 to the PU 114, and LEDs 126 and the status indicator 28 provide information to the operator (not shown in FIG. 6) such as whether the PU 114 has enabled the shock-delivery-and-ECG-front-end circuit 118 to deliver a shock to the patient (not shown) or when the recharge battery 44 needs to be replaced. A contrast button 128 allows the operator to control the contrast of the display screen 24 if present, and a memory such as a read only memory (ROM) 130 stores programming information for the PU 114 and the gate arrays 116 and 120.

The AED circuit 110 and other similar AED circuits that may incorporate the PM circuit 112 are discussed in the following references, which are incorporated by reference: U.S. Pat. No. 5,836,993, U.S. Pat. No. 5,735,879 entitled ELECTROTHERAPY METHOD AND APPARATUS, U.S. Pat. No. 5,607,454 entitled ELECTROTHERAPY METHOD AND APPARATUS, and U.S. Pat. No. 5,879,374 entitled DEFIBRILLATOR WITH SELF-TEST FEATURES.

Figure 7:
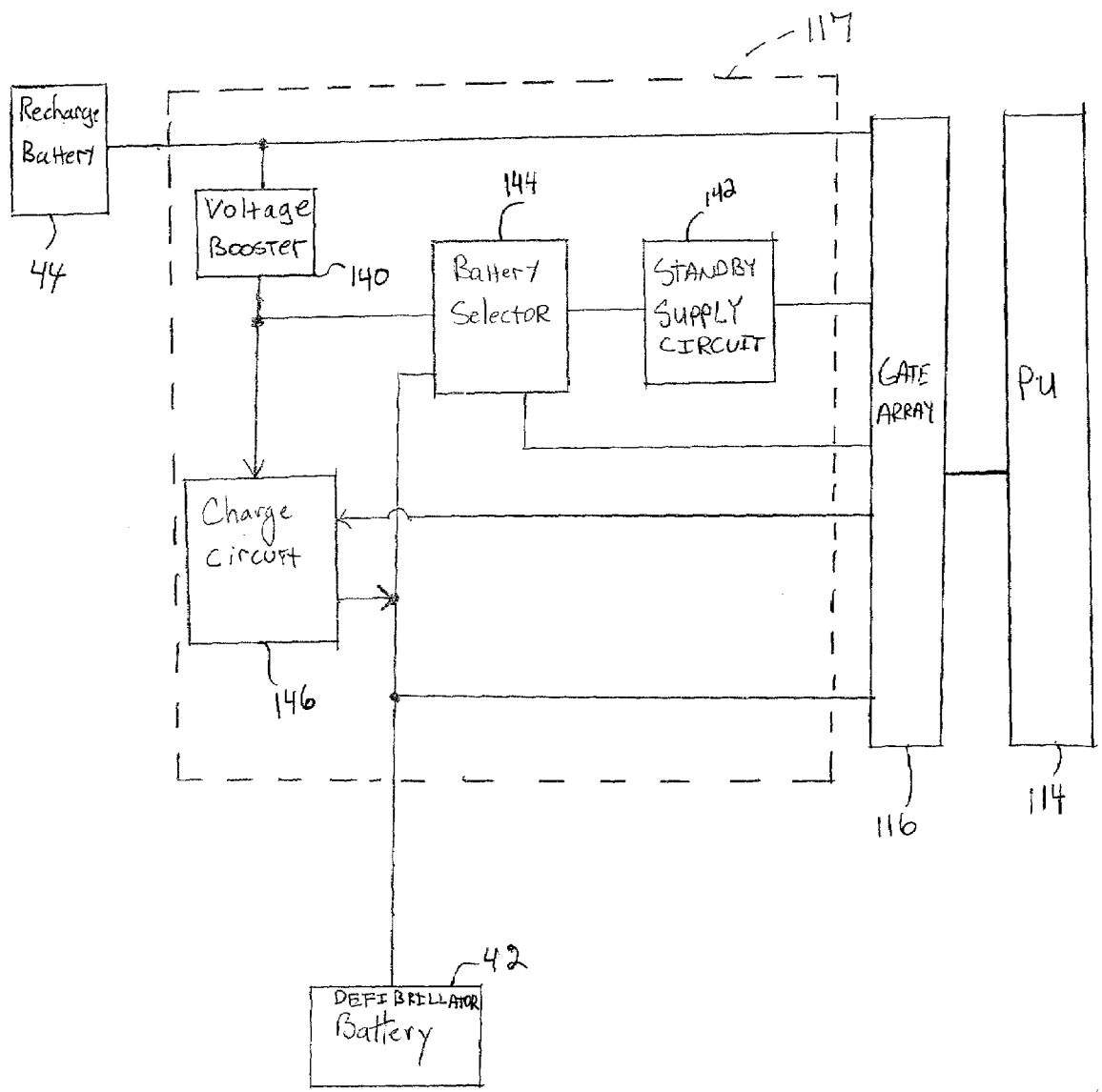
FIG. 7 is a block diagram of the battery charger of FIG. 6 according to an embodiment of the invention.

FIG. 7 is a block diagram of the battery charger 117 of FIG. 6 according to an embodiment of the invention, and of other circuits and components of the circuit 110 that interact with the charger. The charger 117 includes a voltage booster 140, a supply circuit 142 for powering the charger 117 and other circuits of the circuit 110 during charging of the battery 42, a battery selector 144 for selecting the battery—recharge or defibrillator—to power the supply circuit 142, and a charge circuit 146 for charging the battery 42. There are many conventional designs for the booster 140, supply circuit 142, selector 144, and charge circuit 146 that are suitable for use in the battery charger 117. Therefore, detailed discussions of these circuits are omitted for brevity.

In operation, the battery charger 117 uses the recharge battery 44 to maintain a predetermined charge level on the defibrillator battery 42. Specifically, the PU 114 monitors the voltage across the defibrillator battery 42 via the gate array 116. If this voltage is below a recharge level, for example 3.5 volts (V), then the PU 114 activates the charge circuit 146 to charge the defibrillator battery 42 with energy from the recharge battery 44. When the voltage across the defibrillator battery 42 surpasses a charged level, for example 3.9 V, the PU 114 deactivates the charge circuit 146. The PU 114 also monitors the voltage across the recharge battery 44 via the gate array 116, and, as discussed above in conjunction with FIGS. 2 and 6, generates an alarm signal to indicate that the battery 44 needs to be replaced if this voltage is below a predetermined level.

The battery selector 144 connects the recharge battery 44 to circuits that are needed during the recharge operation if the voltage across the defibrillator battery 42 is too low to power these circuits. As stated above, the PU 114 monitors the voltage across the defibrillator battery 42. If this voltage falls below a low-power level, for example 3.3 V, then the PU 114 causes the battery selector 144 to couple the recharge battery 44 to the supply circuit 142. When the voltage increases above the low-power level, the PU 114 causes the battery selector 144 to couple the defibrillator battery 42 to the supply circuit 142. Such a low-power situation may occur if the recharge battery 44 is depleted and is not replaced soon enough to maintain an adequate charge on the defibrillator battery 42. Without the battery selector 144, such a situation would render the battery recharger 117 inoperable until the defibrillator battery 42 was replaced. Consequently, the battery selector 144 avoids this inconvenience by powering the battery recharger 117, the PU 114, and other circuits with the recharge battery 44 until the voltage across the defibrillator battery 42 is high enough to power these circuits.

The voltage booster 140 boosts the voltage across the recharge battery 44 to a level that is high enough to charge the defibrillator battery 42. For example, if the recharge battery 44 is a 1.5 V AA battery, then the booster 140 may boost the 1.5 V to 4.5 V so that the charge circuit 146 can charge the battery 42 to 3.9 V. But if the voltage across the recharge battery 44 is high enough to charge the defibrillator battery 42, then the booster 140 may be omitted. Moreover, if the voltage across the defibrillator battery 42 is too high, then one may replace the booster 140 with a down converter (not shown) to reduce the voltage to a level suitable for charging the defibrillator battery 42.

FIG. 8 is a diagram of a fuel cell 160 of a fuel-cell system (FIGS. 9–10) that can be used in place of one or more of the batteries 42 and 44 (FIG. 2), 66 (FIG. 3), 42 and 76 (FIG. 4), and 102 (FIG. 5) as discussed above in conjunction with FIGS. 2–5. The fuel cell 160 combines a fuel, such as methane, hydrogen gas, or methanol, with an oxidant to generate electric power. The cell 160 includes an anode 162 (+) and a cathode 164 (−) and a proton-exchange membrane 166 that allows the fuel and oxidant—the oxidant is typically oxygen from the air, although pure oxygen or other oxidants can be used—to combine and generate voltage V across the anode and cathode. Intakes 168 and 170 respectively provide the oxygen and fuel to respective sides of the membrane 166, and a vent 172 allows the byproducts—typically water—of the fuel and oxygen to escape from the interior of the cell 160. When a load 174 is connected between the terminals 176 and 178, a current flows from the anode 162, through the load 174, to the cathode 164.

FIG. 9 is a diagram of a fuel-cell system 180 that includes the fuel cell 160 of FIG. 8. The system 180 includes a fuel reservoir 182 that is remote from the cell 160 and a connector 184 for coupling the reservoir's outlet 186 to the cell's fuel intake 170. The system 180 can be used in conjunction with the AED system 36 (FIG. 2), where the cell 160 is located in the AED 38 and the reservoir 182 is located in the cartridge 42.

FIG. 10 is a diagram of a fuel-cell system 190 that includes the fuel cell 160 of FIG. 8. The system 190 includes a fuel reservoir 182 that is connected to or integrated with the cell 160. The reservoir's outlet 192 is integral with the cell's fuel intake 170 or is connected thereto with a connector (not shown in FIG. 10). The system 190 can be used in conjunction with the AED system 60 (FIG. 3), where the system 190 is located in the cartridge 64. Alternatively, the system 190 can be used in conjunction with the AED system 70 (FIG. 4), where the system 190 is located in the AED 72.

What is claimed is:

1. A cartridge for a defibrillator, the defibrillator including a rechargeable battery and a shock delivery circuit coupled to the rechargeable battery, the cartridge comprising:
   a housing having an interior and removably attachable to the defibrillator;
   an electrode pad disposed within the interior; and
   a power source disposed within the interior and coupled to the rechargeable battery when the housing is attached to the defibrillator,
   wherein the power source is operable to provide power to charge the rechargeable battery of the defibrillator.

2. The cartridge of claim 1 wherein the power source comprises a battery.

3. The cartridge of claim 1 wherein the power source comprises an alkaline battery.

4. The cartridge of claim 1 wherein the power source comprises a lithium ion battery.

5. The cartridge of claim 1 wherein the power source comprises an alkaline battery and a lithium ion battery.

6. The cartridge of claim 1 wherein the power source comprises a fuel cell.

7. A defibrillator system comprising:
   a defibrillator including a shock delivery circuit,
   wherein the defibrillator comprises a rechargeable battery coupled to the shock delivery circuit; and
   a cartridge comprising:
   a cartridge housing having an interior and removably attachable to the defibrillator;
   an electrode pad disposed in the interior of the housing;
   a power source disposed in the interior of the housing, and
   wherein the power source is operable to recharge the battery with power provided by the power source when the housing is attached to the defibrillator.

8. The defibrillator system of claim 7
   wherein the power source comprises a battery and is operable to maintain a predetermined charge on the rechargeable battery using the power provided by the power source.

9. A defibrillator system comprising:
   a defibrillator for generating a defibrillation shock; and
   a field-replaceable component that is attachable to the defibrillator wherein:
   the defibrillator comprises a battery operable to power the defibrillator; and the field-replaceable component comprises an electrode-pad storage cartridge including,
 a housing having an interior and removably attachable to the defibrillator,
 an electrode pad disposed within the interior, and
 a power source disposed in the interior and operable to charge the battery when the housing is attached to the defibrillator.

* * * * *